United States Patent [19]

Bachy et al.

[11] Patent Number: 5,468,750
[45] Date of Patent: Nov. 21, 1995

[54] HETEROCYCLE-COUPLED SUBSTITUTED PYRROLO[3,2-C]PYRIDIN-2-CARBOXYLIC ACIDS

[75] Inventors: André Bachy, Toulouse; Laurent Fraisse, Jurancon; Peter Keane, Portet sur Garonne; Etienne Mendes, Toulouse; Jean-Claude Vernieres; Jacques Simiand, both of Muret, all of France

[73] Assignee: Elf Sanofi, Paris, France

[21] Appl. No.: 273,943

[22] Filed: Jul. 12, 1994

Related U.S. Application Data

[62] Division of Ser. No. 109,073, Aug. 19, 1993, Pat. No. 5,360,799.

[30] Foreign Application Priority Data

Aug. 27, 1992 [FR] France ............................ 92 10329

[51] Int. Cl.⁶ ................... A61K 31/44; A61K 31/495; C07D 495/14; C07D 495/04
[52] U.S. Cl. ................ 514/255; 514/183; 514/212; 514/232.8; 514/291; 514/293; 540/481; 540/597; 546/80; 546/83; 544/126; 544/361
[58] Field of Search ................... 514/183, 212, 514/232.8, 255, 291, 293; 540/481, 597; 546/80, 83; 544/126, 361

[56] References Cited

FOREIGN PATENT DOCUMENTS 2246271 5/1975 France .

OTHER PUBLICATIONS

J. M. Barker et al., "Thienopyridines. Part 4. Preparation of Some Dithieno(3,2-bi:2i, 3i-d)pyridine Derivatives", Chemical Abstracts, vol. 97, 1982, Abs. No. 144802p, p. 683.
J. M. Barker et al., "Thienopyridines. Part 6. Synthesis & Nucleophilic Substitution of Some Chlorothieno(2, 3–b)pyridine . . . ", Chemical Abstracts, vol. 104, 1986, Abs. No. 5801n, p. 5797.
J. Sharada et al., "Synthesis & Biological Activity of Furoquinolines: 2-Aroyl-4-methyl/4, 6–dimethyl–3–phenylfuro(3,2–c)quinolines", Chemical Abstracts, vol. 108, 1988, Abs. No. 21749q, p. 587.

Primary Examiner—Raymond Henley, III
Assistant Examiner—Phyllis G. Spivack
Attorney, Agent, or Firm—Jacobson, Price, Holman & Stern

[57] ABSTRACT

A compound of formula

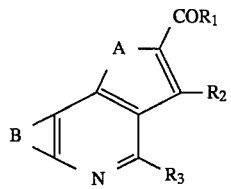

in which

A represents S;

$R_1$ is selected from the group consisting of OH, $(C_1-C_{12})$alkyl, $(C_1-C_{12})$alkoxy, benzyloxy, phenyl, benzyl $(C_1-C_4)$alkyl $NZ_1Z_2$, and $NZ_1Z_2$;

$R_2$ is selected from the group consisting of OH, SH, $(C_1-C_4)$alkoxy, $(C_1-C_4)$alkylthio, and $NZ_1Z_2$;

$R_3$ is selected from the group consisting of H, $(C_1-C_4)$alkyl, $(C_1-C_4)$alkylthio, $(C_1-C_4)$alkoxy, phenyl, and benzyl;

B is selected from the group consisting of phenyl; pyridyl; phenyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_6)$alkyl, formyl, and benzyl or —$NZ_1Z_2$ is selected from the group consisting of pyrrolidinyl, piperidinyl, morpholino, hexahydroazepino,

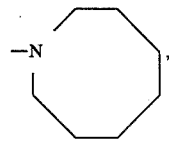

piperazino, piperazino substituted in position 4 by $(C_1-C_8)$alkyl, benzyl or diphenylmethyl; and pyridyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_6)$alkyl, formyl, and benzyl, or $NZ_1Z_2$ is selected from the group consisting of pyrrolidinyl, piperidinyl, morpholino, hyxahydroazepino,

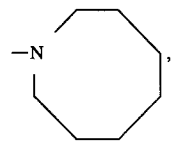

piperazino, and piperazino substituted in position 4 by $(C_1-C_8)$alkyl, benzyl or diphenylmethyl; or its salt with an acid or a base.

6 Claims, No Drawings

HETEROCYCLE-COUPLED SUBSTITUTED PYRROLO[3,2-C]PYRIDIN-2-CARBOXYLIC ACIDS

This application is a divisional of Ser. No. 08/109,073, filed Aug. 19, 1993, now U.S. Pat. No. 5,360,799.

The present invention relates to substituted pyrrolo[3,2-c]pyridin-2-carboxylic acids coupled to an aromatic heterocycle and to their sulphur-containing analogs, to processes for their preparation and to the pharmaceutical compositions which comprise them as active ingredients.

These new compounds are especially inhibitors of the effect of biological oxygenated free radicals, such as the superoxide anion $O_2^-$ or the hydroxyl radical; it is known that when these free radicals, necessarily present in man and animals, are formed in an amount which is too great for them to be rapidly removed by the usual physiological mechanisms, they attack and destroy cell constituents, such as nucleic acids, proteins or walls. The tissues affected are very diverse and many authors regard free radicals as the source of many degenerative diseases ranging from inflammatory or autoimmune diseases to respiratory insufficiency and cardiac, cerebral or intestinal ischemias; they are also implicated in the degenerative phenomena of ageing.

The compounds of the invention correspond to the formula I:

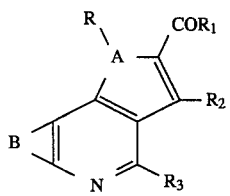

in which $R_1$ represents OH, $(C_1-C_{12})$alkyl, $(C_1-C_{12})$alkoxy, benzyloxy, phenyl, benzyl, $(C_1-C_4)$alkyl$NZ_1Z_2$ or $NZ_1Z_2$;

$R_2$ represents OH, SH, $(C_1-C_4)$alkoxy, $(C_1-C_4)$alkylthio or $NZ_1Z_2$;

$R_3$ represents H, $(C_1-C_4)$alkyl, $(C_1-C_4)$alkylthio, $(C_1-C_4)$alkoxy, phenyl or benzyl;

A represents S, and in this case R represents nothing, or

A represents N and R represents H or $(C_1-C_4)$alkyl which can be substituted by phenyl or $NZ_1Z_2$;

B represents an aromatic ring coupled to the pyridyl ring, and can be phenyl, pyridyl or thienyl to form respectively a pyrrolo[3,2-c]quinoline, pyrrolo[3,2-c]naphthyridine or pyrrolo[3,2-c]thienopyridine tricyclic group when A represents N, or a thieno[3,2-c]quinoline, thieno[3,2-c]naphthyridine or thieno[3,2-c]thienopyridine group when A represents S;

B is optionally substituted by one or more groups chosen from halo, $(C_1-C_6)$alkyl, $(C_1-C_6)$alkoxy, $CF_3$, $CH_2NZ_1Z_2$ or $NZ_1Z_2$; and $Z_1$ and $Z_2$ represent, independently of each other, H, $(C_1-C_6)$alkyl, formyl or benzyl, or they form, with the nitrogen atom to which they are attached, a saturated heterocycle, optionally interrupted by a heteroatom chosen from O, S or N, it being possible for the latter to be substituted by $(C_1-C_8)$alkyl, benzyl, phenyl or diphenylmethyl, with the proviso that when A is S, R is nothing, $R_1$ is —$OCH_3$, $R_3$ is H and B is thienyl, $R_2$ cannot be —OH or —O—$CH_3$;

as well as the salts of these compounds with an acid or a base.

The alkyl and alkoxy groups can be linear or branched or form a ring, especially cyclopentyl or cyclohexyl.

F or Cl are preferred as halogen.

When the group $NZ_1Z_2$ represents a saturated heterocycle, it can be a pyrrolidinyl, piperidinyl, morpholino, hexahydroazepino, piperazino or piperazino substituted in position 4 by $(C_1-C_8)$alkyl, benzyl, phenyl or diphenylmethyl.

Among the compounds of the invention, the preferred ones are those of formula II:

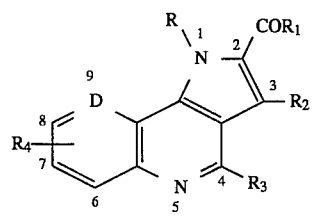

in which R, $R_1$, $R_2$ and $R_3$ are as in Formula I and D represents N or better C, whereas $R_4$ represents $NZ_1Z_2$, and more particularly those in which $R_4$ is at position 8, ortho to D, and, among the last ones, preferably the compounds in which $R_2$ is $NZ'_1Z'_2$, $Z'_1$ and $Z'_2$ representing, independently of each other, H or $(C_1-C_6)$alkyl. Among the latter compounds, those for which $COR_1$ is in addition an ester group are preferred.

Another group of preferred compounds consist of the compounds of formula II in which R, $R_1$, $R_2$ and $R_3$ are as in the formula I and D represents N, whereas $R_4$ represents $NZ_1Z_2$, $Z_1$ and $Z_2$ representing, independently of each other, H or $(C_1-C_6)$alkyl or $Z_1$ and $Z_2$ forming, with the nitrogen atom to which they are attached, a piperazino group which can be substituted on the nitrogen by $(C_1-C_8)$alkyl, phenyl or diphenylmethyl.

The compounds of formula I can be prepared, by using processes whose principles are known in themselves, from suitably substituted quinolines, naphthrydines or thienopyridines.

According to one process, the compound of formula

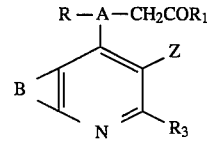

in which A, B, R, $R_1$ and $R_3$ have the same meaning as in the formula I, and Z represents an alkoxycarbonyl or cyano group, is cyclised, in a Dieckmann reaction, to give a compound of formula I in which R2 represents OH, when Z represents an alkoxycarbonyl group, or to give a compound of formula I in which $R_2$ represents $NH_2$, when Z represents a cyano group.

According to another process, the compounds of formulae

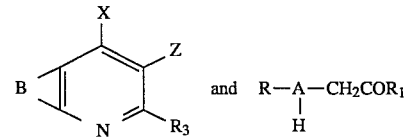

in which A, B, R, $R_1$ and $R_3$ have the same meaning as in the formula I, X represents Cl and Z represents an alkoxycarbonyl or cyano group, are heated, in the presence of phenol, to form a compound of formula I in which $R_2$ represents OH, when Z represents an alkoxycarbonyl group, or to form a compound of formula I in which $R_2$ represents $NH_2$, when Z represents a cyano group.

In order to produce the substituted pyrroles of formula I in which A is N and $R_2$ is OH, an amine of formula III:

    III in which R and $R_1$ have the same meaning as in the formula I, with the exception of $R_1$=OH, is reacted with the compound of formula IV:

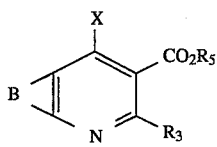    IV in which X represents Cl or Br, $R_5$ represents $(C_1-C_3)$alkyl and B and $R_3$ have the same meaning as in the formula I, to produce the compound of formula V:

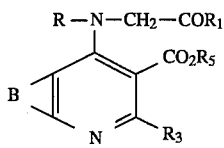    V in which R, $R_1$, $R_3$, $R_5$ and B are as in the formulae III and IV, which compound is cyclised in a Dieckmann reaction by reacting with an organic or inorganic base, such as $(C_2H_5)_3N$, $C_2H_5ONa$, $t-C_4H_9ONa$, NaH or KOH, in a non-aqueous solvent, such as an alcohol, an ether such as dioxane, or dimethylformamide, preferably at a temperature between 0° C. and 80° C.

In order to obtain the substituted pyrroles of formula I in which A is N and $R_2$ is $NH_2$, an amine of formula III is reacted with a compound of formula VI:

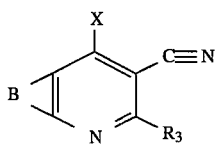    VI in which X is Cl or Br, and $R_3$ and B have the same meaning as in formula I, to produce the compound of formula VII:

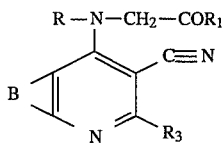    VII in which R, $R_1$, $R_3$ and B are as in the formula I, which compound is cyclised by a Dieckmann reaction.

It is also possible to directly obtain the compounds of formula I by reacting coupled pyridines of formula IV or VI and amines of formula III in the presence of one molar equivalent of phenol and one molar equivalent of an organic or inorganic base, generally without a solvent, at a temperature greater than approximately 100° C.

When, in the compound of formula I which it is desired to obtain, R is other than H, it is possible to substitute the nitrogen of the pyrrole of the compound of formula I in which R=H by reacting with a halide RX in the presence of a strong base, such as NaH, in a polar aprotic solvent or in a 2-phase medium in the presence of a phase transfer catalyst.

In order to obtain the thiophene compounds of formula I in which A represents S, a substituted compound of formula $HS—CH_2—COR_1$, (in place of the amine $RNHCH_2—COR_1$ of formula III) is reacted with the compound of formula IV or with that of formula VI.

In order to obtain the compounds of formula I in which $R_1$ is OH, the corresponding esters in which $R_1$ is alkoxy, for example tert-butoxy, are hydrolysed, preferably in aqueous acidic medium, whereas, in order to obtain the compounds in which $R_1$ is $NZ_1Z_2$, it is possible to react the amine $HNZ_1Z_2$ with the corresponding ester under the usual conditions for producing secondary or tertiary amides; however, it is preferable to directly react the amide of formula III: $RNHCH_2—CONZ_1Z_2$ with the compound of formula IV.

The compounds of formula I in which $R_2$ represents alkoxy are prepared from those in which $R_2$ is OH by reacting with a suitable alkyl halide in the presence of a strong base, such as NaH or $C_2H_5ONa$, under the usual conditions for production of an ether, optionally after protecting the nitrogen of the pyrrole.

The compounds of formula I in which $R_2$ represents $NZ_1Z_2$ with $Z_1$ and $Z_2$ other than H are prepared by known methods for substituting aliphatic primary amines.

The coupled pyridines of formulae IV or VI are prepared from amines $BNH_2$ by conventional methods described for instance in J. Med. Chem., 22, 816–823 (1979) via the corresponding hydroxylated derivatives of formulae IV or VI in which X represents OH, which give, for example, the compound in which X=Cl by reacting with $POCl_3$.

The compounds of formula VIII:

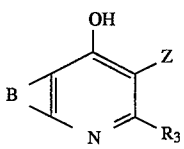    VIII in which Z represents an ethoxycarbonyl or cyano group, can be prepared according to the following reaction scheme:

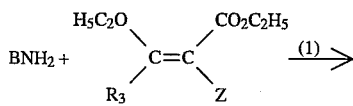

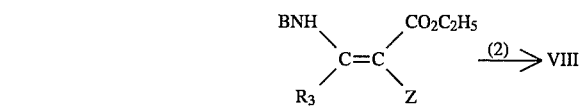

The first stage is generally carried out without a solvent whereas the cyclisation is carried out in a solvent with a very high boiling point, Dowtherm® or diphenyl ether.

Certain of the substituted compounds of formulae V and VII which derive therefrom have been described in EP-A-0,205,362 and EP-A-0,346,208. The others can be prepared by analogous procedures. A process for the preparation of amino ketones of formula III is described especially in Tetrahedron Letters, 25, 2977–2980 (1984); amino esters are well known compounds.

The pharmaceutical compositions which contain, as active ingredients at least one compound of formula I or one of their salts with a pharmaceutically acceptable acid are also provided by the invention. These compositions may contain the carrier conventionally used for formulating pharmaceutical compositions which can be administered orally or rectally or by intravenous or intramuscular injection.

For oral administration, in the form of tablets, gelatin capsules or granules, or even of syrups the unit dose will be between 5 and 200 mg, according to the potency of the compound, the nature of the disease to be treated and the condition of the patient.

For parenteral administration, water-soluble salts of the compounds of formula I will preferably be used or, failing that, products known as solubilisation adjuvants will be introduced into the composition; the unit dose will then be between 1 mg and 30 mg for a volume of 1 to 5 $cm^3$.

The pharmaceutical compositions according to the invention will be administered preventively or curatively in man or animals to reduce or suppress the toxic consequences of the presence of oxygenated free radicals and to treat the disorders which result therefrom. The latter affect varied organs and the compositions of the invention could be used in the treatment of rheumatic diseases such as arthritis, of pulmonary diseases, of cardiovascular diseases such as arteriosclerosis or the consequences of ischemias, of eye disorders such as cataracts, or even cerebral damages, including Alzheimer's disease. For information on the many potential therapeutic uses of these compounds, reference can be made to recently published books and articles, especially to: "Free Radicals in Molecular Biology, Ageing and Disease", published by Raven Press (New York), or to "CRC Handbook of Free Radicals and Antioxidants in Biomedicine", published by CRC Press (Boca Raton, Fla., U.S.A.).

Nevertheless, the therapeutic uses of the compounds according to the invention should not be limited to the indications mentioned; the compounds could be used preventively or curatively in any situation where an excess of oxygenated free radicals can disturb the normal physiological state.

The activity of compounds according to the invention on biological oxygenated free radicals has been established in vitro and in vivo.

In vitro, their action has been studied on the production of malondialdehyde during the decomposition of the endoperoxides resulting from the oxidation, in the presence of iron salt, of the polyunsaturated fatty acids contained in the phospholipids of cell walls. A conventional method, described for instance in CRC Handbook of Methods for Oxygen Radical Research, pp. 203–207 (1985), CRC Press, Boca Raton (Fla., U.S.A.) was used.

In vivo, it was shown that these compounds counteracted the toxic effects of potassium cyanide in mice and reduced hyperglycaemia due to the administration of alloxan in mice.

In effect, it is accepted that, during poisoning with KCN, the cell disorders and the nervous disorders are the consequence of a rise in intracellular calcium, but also of the oxidation of lipid walls of brain cells, and the antagonism of the toxicity of KCN has been used, especially in J. Med. Chem., 33, 1145–1151 (1990) and Arzneim. Forsch., Drug Research 39, 445–450 (1989), to point out an antioxidising activity in the brain.

Moreover, it is known that the administration of alloxan to an animal results in hyperglycaemia due to the destruction of the beta cells of the pancreas by oxygenated radicals, whose formation is triggered by the presence of alloxan, and it has been shown, especially in Biochem. Pharmacol., 34, 3601–3603 (1985) and Fundamental Clinical Pharmacology, 3, 323–328 (1989), that several scavengers of oxygenated free radicals counteract this hyperglycaemia.

In the malondialdehyde test, the 50% inhibitory concentration ($IC_{50}$) is, for the compounds of the invention, generally between 0.1 µM and 10 µM. In the potassium cyanide test, the effective dose 50 ($ED_{50}$) is between approximately 2 mg/kg and 30 mg/kg intravenously in mice, whereas, in the alloxan test, it is between 0.1 mg/kg and 10 mg/kg intravenously in mice.

Examples of the invention are described in the following with, for some of them, their detailed method of preparation.

EXAMPLE 1

Ethyl 1H-3-hydroxypyrrolo[3,2-c]quinoline-2-carboxylate
(A=N; B=$C_6H_4$; R=H; $R_1$=$OC_2H_5$; $R_2$=OH; $R_3$=H)

6 g of ethyl 3-ethoxycarbonyl-4-quinolyl-2-amino acetate (M.p. = 114° C.) in solution in 80 ml of dry toluene are added, over 30 minutes, to 2.5 g of potassium tert-butoxide in 80 ml of anhydrous tert-butanol.

The mixture is stirred for 10 hours under nitrogen and then poured into 200 ml of ice-cold water. An N aqueous HCl solution is introduced into the basic aqueous phase to a pH of 8. The precipitate which appears is filtered, washed with absolute ethanol and then recrystallised from a dimethylformamide/ethanol (50/50) mixture. The crystals are dried at 130° C. under vacuum. Yield 30% - M.p.>250° C.

EXAMPLE 2

8-Chloro-2-(N,N-dipropylcarbamoyl)-3-hydroxy-1-methylpyrrolo[3,2-c]quinoline (A=N; B=8-$ClC_6H_3$; R=$CH_3$; $R_1$=$N(C_3H_7)_2$; $R_2$=OH, $R_3$=H)

0.66g of potassium tert-butoxide is added portionwise to 1.94 g of ethyl 6-chloro-4-(N-(N,N-dipropylcarbamoylmethyl)-N-methylamino)quinoline-3-carboxylate in solution in 30 ml of tetrahydrofuran; the mixture is stirred for 2 hours and then the whole is concentrated to dryness. The precipitate is solubilised in water; the aqueous phase is acidified by addition of an N aqueous HCl solution to a pH of 7. The expected product precipitates; it is purified by recrystallisation from ethyl acetate; M.p.=180° C. (Yield 58%).

EXAMPLE 3

8-(N,N-diethylamino)-2-(N,N-dipropylcarbamoyl)-3-hydroxy-1-methylpyrrolo[3,2-c]quinoline
(A=N; B=8-$(C_2H_5)_2NC_6H_3$; R=$CH_3$;
$R_1$=$N(C_3H_7)_2$; $R_2$=OH)

4.42 g of ethyl 6-(N,N-diethylamino)-4-(N-(N,N-dipropylcarbamoylmethyl)-N-methylamino)quinoline-3-carboxylate, in solution in 100 ml of toluene, are added under nitrogen to a solution of 20 ml of tert-butanol and 1.12 g of potassium tert-butoxide. The mixture is stirred overnight at room temperature and then poured into 250 ml of ice-cold water. The aqueous solution is washed with ether and acidified with dilute HCl to a pH of 7.1–7.2. The pale-yellow precipitate obtained is recrystallised from ethyl acetate; M.p.=224° C. (Yield 40%).

EXAMPLE 4

Ethyl 1H-8-chloro-3-hydroxypyrrolo[3,2-c][1,5]naphthyridine-2-carboxylate

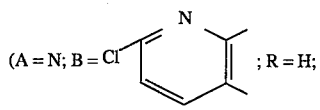

(A = N; B = Cl ; R = H;

$R_1 = OC_2H_5; R_2 = OH; R_3 = H$)

a) Ethyl(6-chloro-3-ethoxycarbonyl-1,5-naphthyridine-4-yl-2-amino)acetate.

5.2 ml of triethylamine are added dropwise to 5.1 g of 4,6-dichloro-3-ethoxycarbonyl-1,5-naphthyridine, in solution in 140 ml of ethanol, and 2.65 g of the hydrochloride of the ethyl ester of glycine.

On completion of addition, the reaction mixture is maintained at the reflux temperature of the ethanol for 2 hours and is then brought to dryness; the residue is dissolved in methylene chloride and the organic phase is washed with water and then dried. After removing the solvent, the product is recrystallised from ethanol. M.p.=140° C. (Yield 46%).

b) 3.84 g of the above naphthyridine, in solution in 45 ml of toluene and 40 ml of dimethylformamide, are added dropwise, under a slight nitrogen stream, to 1.37 g of potassium tert-butoxide in solution in 25 ml of tert-butanol. The solution is stirred at room temperature overnight and the reaction mixture is then poured into 150 ml of a water/ice mixture. After neutralisation of the aqueous phase, the expected product precipitates. M.p.=250° C. (Yield 59%).

EXAMPLE 5

7-(N,N-dipropylcarbamoyl)-6-hydroxy-8-methyl-pyrrolo[3,2-d]thieno[3,2-b]pyridine

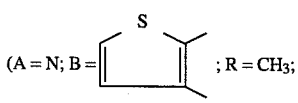

(A = N; B = ; R = CH₃;

$R_1 = N(C_3H_7)_2; R_2 = OH; R_3 = H$)

a) Ethyl 7-(N-(N,N-dipropylcarbamoylmethyl)-N-methylamino)thieno[3,2-b]pyridine-6-carboxylate.

3 g of ethyl 7-chlorothieno[3,2-b]pyridine-6-carboxylate (M.p.=84° C.), prepared by reacting POCl₃ with ethyl 7-hydroxythieno[3,2-b]pyridine-6-carboxylate, obtained by the method described in J. Chem. Res. (M), p. 4701 (1978), 2.6 g of N,N-dipropyl-2-(methyl-amino)acetamide and 2.3 ml of triethylamine in 70 ml of toluene are maintained at the reflux temperature of the mixture for 20 hours. The toluene phase is washed with water and then concentrated to dryness. The expected product is purified by chromatography on silica gel, the eluent being isopropyl ether; it is a yellow oil. (Yield=49%).

b) 2.3 g of the above product, in solution in 50 ml of dry toluene, are introduced into 20 ml of tert-butanol containing 0.8 g of potassium tert-butoxide. After 3 hours at room temperature, the mixture is poured into 300 ml of cold water. The separated aqueous phase is filtered and acidified by addition of a 0.1N aqueous HCl solution to a pH of 7.2. The precipitate formed is filtered and then recrystallised from ethyl acetate. M.p.=120° C. (Yield 40%).

EXAMPLE 6

Ethyl 1H-3-amino-8-(N,N-diethylamino)-6-methyl-pyrrolo[3,2-c]quinoline-2-carboxylate

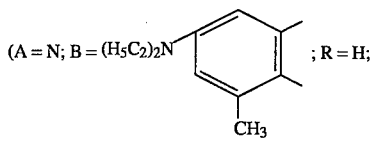

(A = N; B = (H₅C₂)₂N ; R = H;

$R_1 = OC_2H_5; R_2 = NH_2; R_3 = H$).

a) Ethyl 3-[4-(N,N-diethylamino)-2-methylanilino]-2-cyanoacrylate

A mixture of 85 g of 4-(N,N-diethylamino)-2-methylaniline and 67 g of 2-cyano-3-ethoxyacrylate is heated for 2 hours at 140°–150° C. the ethanol being distilled off as it is formed. After recrystallisation from cyclohexane, the desired product is obtained. M.p.=128° C. (Yield 93%).

b) 3-cyano-6-(N,N-diethylamino)-4-hydroxy-8-methylquinoline 60 g of the above product are introduced into 645 ml of diphenyl ether, maintained at 200° C., and then the mixture is heated to 257° C. over 4 hours before distilling approximately 400 ml of diphenyl ether. After cooling, the expected product is precipitated by addition of petroleum ether; the solid is washed with ethyl ether and then with hot ethyl acetate to give a brown solid. M.p.≧250° C. with a yield of 43%.

c) 4-Chloro-3-cyano-6-(N,N-diethylamino)-8-methylquinoline

A mixture of 12 g of the product obtained in b) and 70 ml of phosphoryl chloride is heated for 1 h 30° at 70° C. After evaporation under vacuum of the excess acid chloride, the mixture is poured into water, neutralised and the expected chlorinated product is extracted with methylene chloride. It is purified by filtration through silica gel in a cyclohexane/ethyl acetate (5/5) mixture and recrystallised from petroleum ether. M.p.=115° C. (Yield 44%).

d) A mixture of 5.8 g of the product obtained in c), 4.2 g of phenol, 4.2 g of the hydrochloride of the ethylester of glycine and 8.6 ml of triethylamine are maintained for 2 hours at 140° C.

Water is then added to the mixture, acidification is carried out, the mixture is washed with ethyl ether and then the aqueous phase is neutralised before being extracted with methylene chloride. The residue obtained by evaporation of the solvent is washed with isopropyl ether and then recrystallised from ethyl acetate. M.p.=256° C. (Yield 51%).

EXAMPLE 7

Ethyl 3-amino-8-(N,N-diethylamino)-1,6-dimethylpyrrolo[3,2-c]quinoline-2-carboxylate

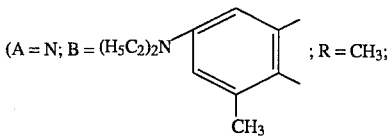

(A = N; B = (H₅C₂)₂N ; R = CH₃;

-continued

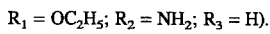

R₁ = OC₂H₅; R₂ = NH₂; R₃ = H).

A mixture of 3,4 g of 4-chloro-3-cyano-6-(N,N-diethylamino)-8-methylquinoline, 2.6 g of phenol and 2.8 g of the hydrochloride of the ethyl ester of sarcosine in 5.1 ml of triethylamine is maintained for 2 hours at 140° C.

After acidification by addition of 0.1N HCl and washing with ethyl ether, the aqueous phase is neutralised and then extracted with methylene chloride. After drying and evaporation of the organic solvent, the residue is chromatographed on silica gel, the eluent being ethyl acetate. The expected product is recrystallised from isopropyl ether. M.p.=209° C. (Yield 36%).

EXAMPLE 8

Ethyl 1H-3-amino-8-(N,N-diethylamino)-4-methylpyrrolo-[3,2-c]quinoline-2-carboxylate

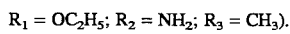

R₁ = OC₂H₅; R₂ = NH₂; R₃ = CH₃).

a) An equimolecular mixture of 4-(N,N-diethylamino)aniline and ethyl 2-cyano-3-ethoxy-3-methylacrylate, prepared by applying the method described in J. Org. Chem., 27, 1371–1374, (1961), is heated for 2 hours at 140° C.
The anilinoacrylate formed is then cyclised in solution in diphenyl ether by heating at 260° C. for 5 hours 30. After the usual treatment, 3-cyano-6-(N,N-diethylamino)-4-hydroxy-2-methylquinoline is obtained with a yield of 49%. M.p.>250° C.
b) 10 g of the quinoline obtained in a) are heated at 70° C. for 1 hour 30 in 50 ml of phosphoryl chloride. After evaporation to dryness, addition of water and neutralisation, extraction is carried out with ethyl acetate; the organic phase is filtered through silica gel to give the desired product with a yield of 53%. M.p.=114° C.
c) 5.8 g of the above chlorinated derivative with 4.17 g of the hydrochloride of the ethyl ester of glycine, 4 g of phenol and 8.3 ml of triethylamine are maintained for 2 hours at 140° C. After acidification and washing with ethyl ether, the aqueous phase is neutralised and then extracted with methylene chloride. The expected product, recrystallised from isopropyl ether, melts at 250° C. (Yield 37%).

EXAMPLE 9

8-(N,N-Diethylamino)-2-(N,N-dipropylcarbamoyl)-3-ethoxy-1-methylpyrrolo[3,2-c]quinoline
(A=N; B=8-(C₂H₅)₂NC₆H₃; R=CH₃;
R₁=N(C₃H₇)₂; R₂ =OC₂H₅; R₃=H).

A solution of 2 g of 8-(N,N-diethylamino)-2-(N,N-dipropylcarbamoyl)-3-hydroxy-1-methylpyrrolo[3,2 -c]quinoline (M.p.=224° C.) in 30 ml of dry dimethyl formamide are introduced, under nitrogen, into 10 ml of the same solvent containing 0.24 g of NaH, and then the mixture is heated at 60° C. for 30 minutes before adding dropwise 0.4 ml of ethyl iodide in solution in 10 ml of solvent. The mixture is heated for 2 hours at 70° C. and then poured into 600 ml of water at around 10° C. By extracting with methylene chloride, there are obtained 2.5 g of crude product which product is purified by chromatography on silica gel, the eluent being ethyl acetate. The oil obtained is dissolved in ethyl ether and a hydrochloric acid solution, in the same solvent, is added to precipitate the hydrochloride of the desired product, with a yield of 65%. M.p.=170° C.

EXAMPLE 10

Ethyl 1H-3-amino-8-(N,N-diethylamino)-4-(methylthio)-pyrrolo[3,2-c]quinoline-2-carboxylate

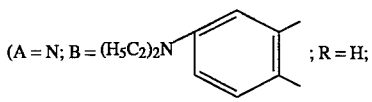

R₁ = OC₂H₅; R₂ = NH₂; R₃ = SCH₃).

a) Ethyl 3-[4-(N,N-diethylamino)anilino]-2-cyano-3-(methylthio)acrylate
21.7 g of ethyl 2-cyano-3,3-bis(methylthio)acrylate and 16.5 g of 4-(N,N-diethylamino)aniline are heated for 2 hours at 120° C. The residue is purified by chromatography on a silica column, the eluent being a toluene/ethanol (97/3) mixture; the expected product is recrystallised from cyclohexane. M.p.=100° C. (Yield 81%).
b) 6-(N,N-diethylamino)-3-cyano-4-hydroxy-2-(methylthio)quinoline
26 g of the product obtained in a) are cyclised by heating in Dowthern A, a mixture of 275 g of biphenyl and 707 ml of diphenyl ether, at the reflux temperature of the mixture for 45 minutes. The solvent is then removed by distillation under reduced pressure. The residue, after washing with petroleum ether, is purified by chromatography on a silica column, the eluent being a toluene/ethanol (95/5) mixture.
c) 6-(N,N-diethylamino)-4-chloro-3-cyano-2-(methylthio)quinoline
100 ml of POCl₃ and 5 g of the oil obtained in b) are heated at reflux for 1 hour. The excess phosphorous oxychloride is removed, the residue is dissolved in dichloromethane and the organic phase is washed with an aqueous NaOH solution and then with water to neutrality; after drying, the organic phase is concentrated to dryness and the residue is purified by chromatography on a silica column (99/1 toluene/ethanol eluent).
After recrystallisation from cyclohexane, the desired product melts at 146° C. (Yield 72%).
d) Ethyl[6-(N,N-diethylamino)-3-cyano-2-methylthio-4-quinolyl]aminoacetate.
2 g of the compound obtained in c), 1 g of the hydrochloride of the ethyl ester of glycine, 2 ml of triethylamine and 100 ml of ethanol are heated at reflux in ethanol for 12 hours before addition of the same amount of hydrochloride and 2 ml of triethylamine. Reflux is maintained for a further 20 hours.
The mixture, after concentration to dryness, is taken up in dichloromethane and the organic phase is washed with water. After removing the solvent, the residue is chromatographed on a silica column (80/20 cyclohexane/ethyl acetate eluent). The expected product is obtained with a yield of 55%, which product melts at 130° C.
e) 1.5 g of this compound are cyclised in 60 ml of ethanol containing sodium ethoxide, obtained with 0.1 g of Na, at room temperature. After stirring for 4 hours, the mixture is concentrated to dryness and 100 ml of water are poured onto the residue. The precipitate is isolated. M.p.=198° C. (Yield 30%).

The melting points of pyrrole derivatives according to the invention, prepared by applying one of the above methods, are mentioned in the following Tables 1 and 2.

TABLE 1

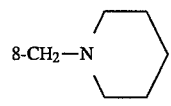

| Example | R | $R_1$ | $R_2$ | $R_3$ | $R_4$ | $R_5$ | M.p. °C. (salt) |
|---|---|---|---|---|---|---|---|
| 11 | H | $OC_2H_5$ | OH | H | 7-Cl | H | >250 |
| 12 | H | $OC_2H_5$ | OH | H | 8-Cl | H | >250 |
| 13 | H | $OC_2H_5$ | OH | H | 8-$CH_3$ | H | >250 |
| 14 | H | $OC_2H_5$ | OH | H | 7-$CF_3$ | H | >250 |
| 15 | H | $OC_2H_5$ | OH | H | 7-F | H | >250 |
| 16 | $CH_3$ | $OC_2H_5$ | OH | H | H | H | 230 (HCl) |
| 17 | $CH_3$ | $OC_2H_5$ | OH | H | 8-Cl | H | 180 |
| 18 | $CH_3$ | $OC_2H_5$ | OH | H | 7-$CF_3$ | H | 170 |
| 19 | H | $OC_2H_5$ | OH | $CH_3$ | H | H | 241 |
| 20 | H | $OC_2H_5$ | OH | $CH_3$ | 8-Cl | H | >250 |
| 21 | H | $OC_2H_5$ | OH | $C_6H_5$ | 8-Cl | H | >250 |
| 22 | H | $OC_2H_5$ | OH | H | 8-$N(C_2H_5)_2$ | H | 160 |
| 23 | H | $OC_2H_5$ | OH | H | 8-$CH_2$—N(piperidine) | H | 158 (HCl) |
| 24 | H | $OC_2H_5$ | OH | H | 8-N(N-methylpiperazine)$NCH_3$ | H | 163 |
| 25 | $CH_2C_6H_5$ | $OC_2H_5$ | OH | H | H | H | 230 (HCl) |
| 26 | $CH_2C_6H_5$ | $OC_2H_5$ | OH | H | 8-Cl | H | 188 |
| 27 | $CH_3$ | $OC_2H_5$ | OH | H | 8-$N(C_2H_5)_2$ | H | 168 (HCl) |
| 28 | $CH_3$ | $OC_2H_5$ | OH | H | 8-N(piperazine)$NCH_3$ | H | 176 |
| 29 | $CH_3$ | $OC_2H_5$ | OH | H | 8-N(piperazine)$NC_7H_{15}$ | H | 158 |
| 30 | H | $CH(C_3H_7)_2$ | OH | H | 8-Cl | H | >250 |
| 31 | H | $CH(C_3H_7)_2$ | OH | H | 8-$N(C_2H_5)_2$ | H | >250 |
| 32 | H | $CH(C_3H_7)_2$ | OH | H | 8-$CH_2$N(piperidine) | H | 171 |
| 33 | H | $C_6H_5$ | OH | H | 8-Cl | H | >250 |
| 34 | H | $C_6H_5$ | OH | H | 8-$N(C_2H_5)_2$ | H | >250 |
| 35 | H | $O(CH_2)_{11}CH_3$ | OH | H | 7-$CF_3$ | H | >250 |
| 36 | $CH_2C_6H_5$ | $OC(CH_3)_3$ | OH | H | H | H | 212 |
| 37 | $CH_3$ | $O(CH_2)_2N(C_2H_5)_2$ | OH | H | 8-Cl | H | 100 |
| 38 | H | $OC_2H_5$ | $NH_2$ | H | 8-Cl | H | >250 |
| 39 | H | $CH(C_3H_7)_2$ | $NH_2$ | H | S-$N(C_2H_5)_2$ | H | >250 |
| 40 | H | $OC_2H_5$ | $NH_2$ | H | 8-$N(C_2H_5)_2$ | H | 232 |
| 41 | H | $OC_2H_5$ | $NH_2$ | H | 8-$N(C_2H_5)_2$ | 7-$CF_3$ | 180 |
| 42 | H | $OC_2H_5$ | $NH_2$ | H | 8-$N(C_2H_5)_2$ | 6-$CF_3$ | >250 |
| 43 | H | $OC_2H_5$ | $NH_2$ | $C_2H_5$ | 8-$N(C_2H_5)_2$ | H | 224 |
| 44 | H | $OC_2H_5$ | $NH_2$ | H | 7-$N(CH_3)_2$ | H | >250 |

TABLE 1-continued

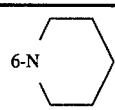

| Example | R | $R_1$ | $R_2$ | $R_3$ | $R_4$ | $R_5$ | M.p. °C. (salt) |
|---|---|---|---|---|---|---|---|
| 45 | H | $OC_2H_5$ | $NH_2$ | H | 6-N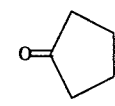 | H | >250 (2HCl) |
| 46 | H | $OCH_2C_6H_5$ | $NH_2$ | $CH_3$ | $8-N(C_2H_5)_2$ | H | 240 |
| 47 | H | $OC(CH_3)_3$ | $NH_2$ | $C_2H_5$ | $8-N(C_2H_5)_2$ | H | 240 |
| 48 | $CH_3$ | $OC_2H_5$ | $NH_2$ | H | $8-N(C_2H_5)_2$ | H | 169 |
| 49 | $CH_3$ | $OC_2H_5$ | $NH_2$ | $C_2H_5$ | $8-N(C_5H_5)_2$ | H | 122 |
| 50 | $CH_3$ | $OC_2H_5$ | $NH_2$ | H | $8-N(C_2H_5)_2$ | $6-CF_3$ | 250 |
| 51 | H | $OCH(CH_3)_2$ | $NH_2$ | H | $8-N(C_2H_5)_2$ | $6-CH_3$ | >250 (HCl) |
| 52 | H | $OCH_2CH(CH_3)_2$ | $NH_2$ | H | $8-N(C_2H_5)_2$ | $6-CH_3$ | 218 |
| 53 | H | $OCH(CH_3)_2$ | $NH_2$ | $CH_3$ | $8-N(C_2H_5)_2$ | H | >250 |
| 54 | H | $OC_5H_{11}$ | $NH_2$ | H | $8-N(C_2H_5)_2$ | $6-CH_3$ | 197 (0.5H$_2$O) |
| 55 | H | $OC_2H_5$ | $NH_2$ | H | $8-N(C_2H_5)(C_4H_9)$ | $6-CH_3$ | 238 (H$_2$O) |
| 56 | H | $OC_2H_5$ | $NH_2$ | H | $8-N(C_2H_5)_2$ | $6-CH_3$ | >250 |
| 57 | H | $OC_2H_5$ | $NH_2$ | $CH_3$ | $8-N(C_2H_5)_2$ | $6-CH_3$ | 210 |
| 58 | H | $OCH(C_2H_5)_2$ | $NH_2$ | $CH_3$ | $8-N(C_2H_5)_2$ | $6-CH_3$ | 225 |
| 59 | H | $OCH(CH_3)_2$ | $NH_2$ | $CH_3$ | $8-N(C_2H_5)_2$ | $6-CH_3$ | 246 |
| 60 | H | $OCH(CH_3)(C_2H_5)$ | $NH_2$ | $CH_3$ | $8-N(C_2H_5)_2$ | $6-CH_3$ | 228 |
| 61 | H | $OCH(CH_3)(C_3H_7)$ | $NH_2$ | $CH_3$ | $8-N(C_2H_5)_2$ | $6-CH_3$ | 198 |
| 62 | H | 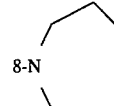 | $NH_2$ | $CH_3$ | $8-N(C_2H_5)_2$ | $6-CH_3$ | 222 (0.5H$_2$O) |
| 63 | H | $OC_2H_5$ | $NH_2$ | $CH_3$ | $8-N(C_2H_5)_2$ | 7-F | 258 |
| 64 | H | $OC_2H_5$ | $NH_2$ | H | $S-N(C_2H_5)_2$ | 7-F | 228 |
| 65 | H | $OC_2H_5$ | $NH_2$ | $CH_3$ | $8-N(C_2H_5)_2$ | 7-Cl | 254 |
| 66 | H | $OC_2H_5$ | $NH_2$ | H | $8-N(C_2H_5)_2$ | 7-Cl | 185 (0.5H$_2$O) |
| 67 | H | $OC_2H_5$ | $NH_2$ | $CH_3$ | $8-N(C_2H_5)_2$ | $6-CF_3$ | 175 |
| 68 | $C_3H_7$ | $OC_2H_5$ | $NH_2$ | H | $8-N(C_2H_5)_2$ | $6-CH_3$ | 136 |
| 69 | H | $OCH(CH_3)_2$ | $NH_2$ | $C_2H_5$ | $S-N(C_2H_5)_2$ | $6-CH_3$ | 217 |
| 70 | H | $OCH_2ClH5$ | $NH_2$ | H | $8-N(C_2H_5)_2$ | $6-CH_3$ | 218 (0.5H$_2$O) |
| 71 | H | $OC_2H_5$ | $NH_2$ | H | 8-N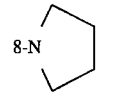 | $6-CH_3$ | >250 (0.5H$_2$O) |
| 72 | H | $OC_2H_5$ | $NH_2$ | H | 8-N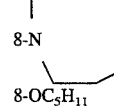 | $6-CH_3$ | >250 (2H$_2$O) |
| 73 | H | $OCH(CH_3)_2$ | $NH_2$ | $CH_3$ | 8-N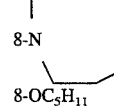 | $6-CH_3$ | 255 |
| 74 | H | $OC_2H_5$ | $NH_2$ | $CH_3$ | $8-OC_5H_{11}$ | H | 244 |
| 75 | H | $OC_2H_5$ | $NHCH_3$ | H | $8-N(C_2H_5)_2$ | H | 224 |
| 76 | H | $OC_2H_5$ | $NHCH_3$ | H | $8-N(C_2H_5)_2$ | $6-CH_3$ | 134 |
| 77 | H | $OC_2H_5$ | $NHCH_3$ | $CH_3$ | $8-N(C_2H_5)_2$ | H | 220 |
| 78 | H | $OC_2H_5$ | $NHC_2H_5$ | H | $8-N(C_2H_5)_2$ | $6-CH_3$ | 226 |
| 79 | H | $OC_2H_5$ | $NHC_3H_7$ | H | $8-N(C_2H_5)_2$ | $6-CH_3$ | 194 |
| 80 | H | $OCH(CH_3)_2$ | $N(C_2H_5)_2$ | $CH_3$ | $8-N(C_2H_5)_2$ | $6-CH_3$ | 182 |
| 81 | H | $OC_2H_5$ | $N(C_3H_7)_2$ | H | $8-N(C_2H_5)_2$ | | 184 |

TABLE 1-continued

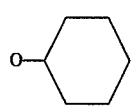

| Example | R | $R_1$ | $R_2$ | $R_3$ | $R_4$ | $R_5$ | M.p. °C. (salt) |
|---|---|---|---|---|---|---|---|
| 82 | H | $OC_2H_5$ | $N(C_2H_5)(CHO)$ | $CH_3$ | $8-N(C_2H_5)_2$ | H | 200 |
| 83 | H | $OCH(CH_3)_2$ | $N(C_2H_5)(CHO)$ | $CH_3$ | $8-N(C_2H_5)_2$ | $6-CH_3$ | 100 |
| 84a | $CH_2C_6H_5$ | $OC_2H_5$ | $NHCH_2C_6H_5$ | H | $8-N(C_2H_5)_2$ | $6-CH_3$ | 182 |
| 84b | H | O–cyclohexyl | $NH_2$ | $CH_3$ | $8-N(C_2H_5)_2$ | $6-CH_3$ | 188 |
| 84c | H | $O-CH(CH_3)-C_3H_7$ | $NH_2$ | $CH_3$ | $8-N(C_2H_5)_2$ | $6-CH_3$ | 210 |
| 84d | H | $OCH(CH_3)_2$ | $NH_2$ | $CH_3$ | $8-N(C_2H_5)_2$ | 7-F | >250 |
| 84e | H | $OCH(CH_3)_2$ | $NH_2$ | $CH_3$ | 8-N(hexamethyleneimino) | $6-CH_3$ | 250 |

TABLE 2

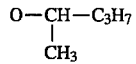

| Example | R | $R_1$ | $R_2$ | $R_3$ | $R_4$ | $R_5$ | M.p. °C. (salt) |
|---|---|---|---|---|---|---|---|
| 85 | $CH_3$ | $N(C_3H_7)_2$ | OH | $SCH_3$ | H | H | 165 |
| 86 | $CH_3$ | $N(C_3H_7)_2$ | OH | H | H | H | 210 |
| 87 | $CH_3$ | $N(C_3H_7)_2$ | OH | H | $7-CF_3$ | H | 228 |
| 88 | $CH_3$ | $N(C_3H_7)_2$ | OH | H | $8-CH_3$ | H | 233 |
| 98 | $CH_3$ | $N(C_3H_7)_2$ | OH | H | $8-C_6H_{11}$ | H | 130 |
| 90 | $CH_3$ | $N(C_3H_7)_2$ | OH | H | $8-CH_3$ | H | 200 |
| 91 | $CH_3$ | $N(C_3H_7)_2$ | OH | H | $8-WH2C_6H_5$ | H | 193 |
| 92 | $CH_2C_6H_5$ | $N(C_3H_7)_2$ | OH | H | 8-Cl | H | 250 |
| 93 | $(CH_2)_2N(C_2H_5)_2$ | $N(C_3H_7)_2$ | OH | H | 8-Cl | H | 220 |
| 94 | $(CH_2)_3N(C_2H_5)_2$ | $N(C_3H_7)_2$ | OH | H | 8-Cl | H | 177 |
| 95 | $C_2H_5$ | $N(C_3H_7)_2$ | OH | H | 8-Cl | H | 230 |
| 96 | $CH_3$ | piperidino | OH | H | H | H | >250 |
| 97 | $CH_3$ | morpholino | OH | H | 8-Cl | H | >250 |
| 98 | $CH_3$ | $N(C_5H_{11})_2$ | OH | H | 8-Cl | H | 185 |
| 99 | $CH_3$ | $N(C_3H_7)_2$ | OH | H | $8-N(C_2H_5)_2$ | H | 224 |

TABLE 2-continued

| Example | R | $R_1$ | $R_2$ | $R_3$ | $R_4$ | $R_5$ | M.p. °C. (salt) |
|---|---|---|---|---|---|---|---|
| 100 | $CH_3$ | $N(C_3H_7)_2$ | OH | H | 8-N-piperidinyl | H | 198 |
| 101 | $CH_3$ | $N(C_3H_7)_2$ | OH | H | 7-$N(CH_3)_2$ | H | 220 |
| 102 | $CH_3$ | $N(C_3H_7)_2$ | OH | H | 8-$CH_2$N-piperidinyl | H | 105 |
| 103 | $CH_3$ | $N(C_3H_7)_2$ | OH | H | 8-$CH_2NC_7H_{15}$ \| $CH_3$ | H | 48 |
| 104 | $CH_3$ | $N(C_3H_7)_2$ | OH | H | 8-N-piperazinyl-$NCH_3$ | H | 156 |
| 105 | $CH_3$ | $N(C_3H_7)_2$ | OH | H | 8-N-piperazinyl-$N(CH_2)_6CH_3$ | H | 104 |
| 106 | $CH_3$ | $N(C_3H_7)_2$ | OH | H | 8-N-morpholinyl-O | H | 150 |
| 107 | $CH_3$ | $N(C_3H_7)_2$ | $OC_2H_5$ | H | H | H | 240 (HCl) |
| 108 | $C_2H_5$ | $N(C_3H_7)_2$ | OH | H | 8-$N(C_2H_5)_2$ | H | >250 (HCl) |
| 109 | $CH_2C_6H_5$ | $N(C_3H_7)_2$ | OH | H | 8-$N(C_2H_5)_2$ | H | >250 (HCl) |
| 110 | H | $N(C_3H_7)_2$ | $NH_2$ | H | B-$N(C_2H_5)_2$ | H | 150 |
| 111 | $CH_3$ | $N(C_3H_7)_2$ | $NH_2$ | H | 8-$N(C_2H_5)_2$ | H | >250 (HCl) |
| 112 | H | N-piperazinyl-$NCH_3$ | $NH_2$ | H | 8-Cl | H | >250 |
| 113 | H | $NH_2$ | $NH_2$ | H | 8-$N(C_2H_5)_2$ | 6-$CH_3$ | >250 |
| 114 | H | $NH_2$ | $NH_2$ | $CH_3$ | 8-$N(C_2H_5)_2$ | 6-$CH_3$ | >250 |

Examples of naphthyridine derivatives are mentioned in Table 3.

TABLE 3

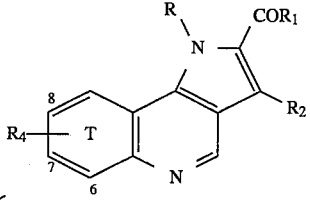

| Example | T | R₄ | R | R₁ | R₂ | M.p. °C. (salt) |
|---|---|---|---|---|---|---|
| 115 | pyridine | 8-N(C₃H₇)₂ | H | OC₂H₅ | OH | 92 (CF₃COOH) |
| 116 | pyridine | 8-N(piperazinyl-NCH₃) | H | OC₂H₅ | OH | 110 |
| 117 | " | 8-N(piperazinyl-NCH₃) | CH₂C₆H₅ | OC₂H₅ | OH | 190 |
| 118 | " | 8-N(piperazinyl-NC₃H₇) | H | OC₂H₅ | OH | >250 |
| 119 | " | 8-N(piperazinyl-NCH₃) | CH₂ | OC₂H₅ | OH | 135 |
| 120 | " | 8-N(piperazinyl-NCH(C₆H₅)₂) | H | OC₂H₅ | OH | 150 |
| 121 | " | 8-N(piperazinyl-NCH₂C₆H₅) | H | OC₂H₅ | OH | 90 |
| 122 | " | 8-N(piperazinyl-NCH(C₆H₅)₂) | CH₃ | OC₂H₅ | OH | 220 |
| 123 | " | 8-N(piperazinyl-NCH₂C₆H₅) | H | OC₂H₅ | OH | 230 |
| 124 | " | 8-N(piperazinyl-NH) | CH₃ | OC₂H₅ | OH | 170 (CH₃COOH) |
| 125 | " | 8-Cl | CH₃ | N(C₃H₇)₂ | OH | 231 |
| 126 | " | 8-N(C₃H₇)₂ | CH₃ | N(C₃H₇)₂ | OH | 118 |
| 127 | " | 8-N(piperazinyl-NCH₃) | CH₃ | N(C₃H₇)₂ | OH | 120 |

TABLE 3-continued

| Example | T | $R_4$ | R | $R_1$ | $R_2$ | M.p. °C. (salt) |
|---|---|---|---|---|---|---|
| 128 | pyridyl-methyl | 7-Cl | H | $OC_2H_5$ | OH | >250 |
| 129 | pyridyl-methyl | | H | $CH_3$ | $N(C_3H_7)_2$ | OH | 175 |
| 130 | pyridyl-methyl | 7-Cl | H | | $N(C_3H_7)_2$ | OH | 225 |
| 131 | " | 7-Cl | $CH_3$ | | $N(C_3H_7)_2$ | OH | 150 |

EXAMPLE 132

1H-3-Amino-2-carbamoyl-8-(N,N-diethylamino)-4-methylpyrrolo[3,2-c]quinoline

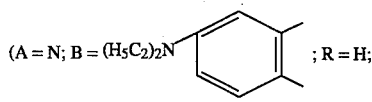

$R_1 = NH_2$; $R_2 = NH_2$; $R_3 = CH_3$)

a) 4-(carbamoylmethylamino)-3-cyano-6-(N,N-diethylamino)-2-methylquinoline 6.5 g of chloroquinoline, prepared as in Example 8 b), 4.55 g of phenol, 3.7 g of glycinamide hydrochloride and 9.3 ml of triethylamine are heated for 2 hours at 140° C. After cooling, the mixture is acidified by addition of a 0.1N aqueous HCl solution; the crystals obtained are washed with ethyl ether and recrystallised from ethanol. M.p.=225° C.

b) 1 g of the above product is added portionwise to 0.4 g of potassium tert-butoxide in 50 ml of tert-butanol. After stirring for 1 hour, the mixture is poured into cold water and then acidified by addition of a dilute aqueous HCl solution. The hydrochloride of the expected product precipitates after washing with hot acetonitrile; it melts at more than 260° C.

EXAMPLE 133

1H-3-Amino-8-(N,N-diethylamino)-4-ethylpyrrolo-[3,2-c]quinoline-2-carboxylic acid

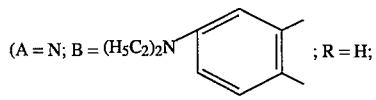

$R_1 = OH$; $R_2 = NH_2$; $R_3 = C_2H_5$)

0.5 g of tert-butyl 1H-3-amino-8-(N,N-diethylamino)-4-ethylpyrrolo[3,2-c]quinoline-2-carboxylate (M.p.=240° C.) are added portionwise to an ethyl acetate solution saturated with gaseous hydrochloric acid. The mixture is stirred at room temperature for 48 hours. The crystals obtained are filtered, and washed with acetonitrile and then with isopropanol. M.p.=223° C.

EXAMPLE 134

Ethyl 8-(N,N-diethylamino)-3-hydroxythieno-[3,2-c]-quinoline-2-carboxylate

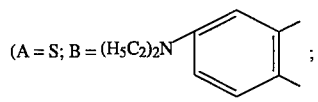

$R_1 = OC_2H_5$; $R_2 = OH$; $R_3 = H$)

a) 6.1 g of ethyl 6-(N,N-diethylamino)-4-chloroquinoline-3-carboxylate, 2.6 g of ethyl thioglycolate and 3 ml of triethylamine in solution in 50 ml of dimethyl formamide are heated for 3 hours at 70° C. The solvent is evaporated and water and ethyl ether are poured onto the residue; after separation of the ether phase, drying and evaporation of the solvent, the residual oil is chromatographed through silica gel to produce, with a yield of 50%, oily ethyl [4-{6-(N,N-diethylamino)-3-ethoxycarbonyl}quinolyl]-2-thioacetate.

b) 1.6 g of this product in solution in 50 ml of toluene are introduced into a solution of 0.5 g of potassium tert-butoxide in 8 ml of tert-butanol. The mixture is stirred for 12 hours before concentrating to dryness. The residue is taken up in water and the aqueous phase is neutralised by addition of a dilute aqueous hydrochloric acid solution. The yellow precipitate formed is filtered and then recrystallised from a mixture of hexane and isopropyl ether (50/50) to give, with a yield of 45%, the expected product which melts at 142° C.

Examples of thienoquinoline and naphthyridine derivatives appear in Table 4.

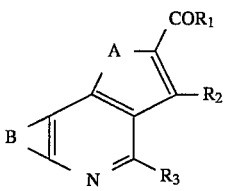

in which

TABLE 4

| Example | (structure) | $R_1$ | $R_2$ | $R_4$ | M.p. °C. |
|---|---|---|---|---|---|
| 135 | $R_4$—(pyridine ring with N) | $OC_2H_5$ | OH | 8-($H_3C$—N⟨  ⟩N—) | >250 |
| 136 | $R_4$—(benzene ring) | $OC_2H_5$ | OH | H | 188 |
| 137 | $R_4$—(benzene ring) | $OC_2H_5$ | OH | 8-(⟨  ⟩$NCH_2$—) | 168 |
| 138 | $R_4$—(benzene ring) | $OC_2H_5$ | OH | 8-($H_3C$—N⟨  ⟩N—) | 210 |
| 139 | $R_4$—(benzene ring) | $N(C_3H_7)_2$ | OH | 8-Cl | 146 |
| 140 | $R_4$—(benzene ring) | $N(C_3H_7)_2$ | OH | 8-$N(C_2H_5)_2$ | 156 |
| 141 | $R_4$—(benzene ring) | $OC_2H_5$ | $NH_2$ | 8-$N(C_2H_5)_2$ | 186 |
| 142 | $R_4$—(benzene ring) | $OC_2H_5$ | OH | 8-$N(C_2H_5)_2$ | 142 |

We claim:

1. A compound of formula

A represents S;

$R_1$ is selected from the group consisting of OH, ($C_1$–$C_{12}$)alkyl, ($C_1$–$C_{12}$)alkoxy, benzyloxy, phenyl, benzyl ($C_1$–$C_4$)alkyl $NZ_1Z_2$, and $NZ_1Z_2$;

$R_2$ is selected from the group consisting of OH, SH, ($C_1$–$C_4$)alkoxy, ($C_1$–$C_4$)alkylthio, and $NZ_1Z_2$;

$R_3$ is selected from the group consisting of H, $(C_1-C_4)$alkyl, $(C_1-C_4)$alkylthio, $(C_1-C_4)$alkoxy, phenyl, and benzyl;

B is selected from the group consisting of phenyl; pyridyl; phenyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_6)$ alkyl, formyl, and benzyl or $—NZ_1Z_2$ is selected from the group consisting of pyrrolidinyl, piperidinyl, morpholino, hexahydroazepino,

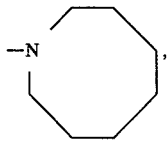

piperazino, piperazino substituted in position 4 by $(C_1-C_8)$alkyl, benzyl or diphenylmethyl; and pyridyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_6)$alkyl, formyl, and benzyl, or $NZ_1Z_2$ is selected from the group consisting of pyrrolidinyl, piperidinyl, morpholino, hexahydroazepino,

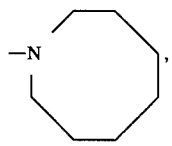

piperazino, and piperazino substituted in position 4 by $(C_1-C_8)$alkyl, benzyl or diphenylmethyl; or its salt with an acid or a base.

2. Pharmaceutical composition which comprises a therapeutically effective amount of a compound according to claim 1, optionally in the form of a salt with a pharmaceutically acceptable acid or base together with a pharmaceutically acceptable carrier.

3. A compound of

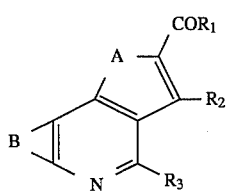

in which

A represents S;

$R_1$ is selected from the group consisting of OH, $(C_1-C_6)$alkyl, $(C_1-C_{12})$alkoxy, phenyl, and $NZ_1Z_2$;

$R_2$ is selected from the group consisting of OH, SH, $(C_1-C_4)$alkoxy, $(C_1-C_4)$alkylthio, and $NZ_1Z_2$;

$R_3$ is selected from the group consisting of H, $(C_1-C_4)$alkyl, $(C_1-C_4)$alkylthio, $(C_1-C_4)$alkoxy, phenyl, and benzyl;

B is selected from the group consisting of phenyl; pyridyl; phenyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_4)$alkyl, and benzyl or $—NZ_1Z_2$ is selected from the group consisting of pyrrolidinyl, piperidinyl, morpholino, hexahydroazepino,

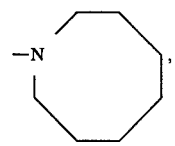

piperazino, piperazino substituted in position 4 by $(C_1-C_8)$alkyl, benzyl or diphenylmethyl; and pyridyl substituted by one or more groups selected from halo, $(C_1-C_6)$alkyl, $(C_1-C_6)$alkoxy, $CF_3$, $CH_2NZ_1Z_2$, and $NZ_1Z_2$ wherein $Z_1$ and $Z_2$ are selected, independently of each other, from the group consisting of H, $(C_1-C_4)$alkyl, and benzyl or $—NZ_1Z_2$ is selected from the group consisting of pyrrolidinyl, piperidinyl, morpholino, hexahydroazepino,

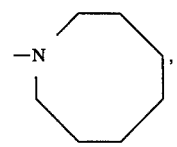

piperazino, and piperazino substituted in position 4 by $(C_1-C_8)$alkyl, benzyl or diphenylmethyl; or its salt with an acid or a base.

4. Pharmaceutical composition which comprises a therapeutically effective amount of a compound according to claim 3, optionally in the form of a salt with a pharmaceutically acceptable acid or base together with a pharmaceutically acceptable carrier.

5. A compound of

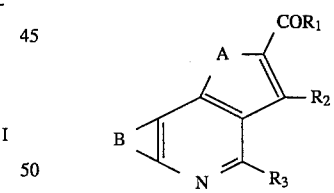

in which

A represents S;

$R_1$ is selected from the group consisting of $(C_1-C_{12})$alkoxy and $NZ_1Z_2$;

$R_2$ is selected from the group consisting of OH and $NZ_1Z_2$;

$R_3$ is H;

B is selected from the group consisting of phenyl; phenyl substituted by one or more groups selected from halo and $NZ_1Z_2$ wherein $Z_1$ and $Z_2$ represent, independently of each other, $(C_1-C_6)$alkyl or $NZ_1Z_2$ is selected from the group consisting of piperidinyl, piperazino, and piperazino substituted in position 4 by $(C_1-C_8)$alkyl; pyridyl; and pyridyl substituted by $NZ_1Z_2$ wherein $NZ_1Z_2$ is selected from piperazino, and piperazino substituted in position 4 by $(C_1-C_8)$alkyl; or its salt with an acid or a base.

6. Pharmaceutical composition which comprises a therapeutically effective amount of a compound according to claim 5, optionally in the form of a salt with a pharmaceutically acceptable acid or base together with a pharmaceutically acceptable carrier.

\* \* \* \* \*